US008137386B2

(12) United States Patent
Jackson

(10) Patent No.: US 8,137,386 B2
(45) Date of Patent: Mar. 20, 2012

(54) POLYAXIAL BONE SCREW APPARATUS

(76) Inventor: Roger P. Jackson, Prairie Village, KS (US)

( * ) Notice: Subject to any disclaimer, the term of this patent is extended or adjusted under 35 U.S.C. 154(b) by 1681 days.

(21) Appl. No.: 10/651,003

(22) Filed: Aug. 28, 2003

(65) Prior Publication Data

US 2005/0049589 A1    Mar. 3, 2005

(51) Int. Cl.
*A61B 17/70*   (2006.01)
(52) U.S. Cl. ........................................ 606/266
(58) Field of Classification Search ............... 606/61, 606/72, 73
See application file for complete search history.

(56) References Cited

U.S. PATENT DOCUMENTS

| | | |
|---|---|---|
| 1,300,275 A | 4/1919 | Johnson |
| 1,330,673 A | 2/1920 | Anderson |
| 2,083,092 A | 1/1936 | Richer |
| 2,201,087 A | 5/1940 | Hallowell |
| 2,239,352 A | 4/1941 | Cherry |
| 2,295,314 A | 9/1942 | Whitney |
| 2,346,346 A | 4/1944 | Anderson |
| 2,362,999 A | 11/1944 | Elmer |
| 2,537,029 A | 8/1946 | Cambern |
| 2,445,978 A | 7/1948 | Stellin |
| 2,531,892 A | 11/1950 | Reese |
| 2,532,815 A | 12/1950 | Kindsvatter |
| 2,553,337 A | 5/1951 | Shafer |
| 2,778,265 A | 1/1957 | Brown |
| 2,813,450 A | 11/1957 | Dzus |
| 2,969,250 A | 1/1959 | Kull |
| 2,877,681 A | 3/1959 | Brown |
| 2,927,332 A | 3/1960 | Moore |
| 3,013,244 A | 12/1961 | Rudy |
| 3,143,029 A | 8/1964 | Brown |
| D200,217 S | 2/1965 | Curtiss |
| 3,370,341 A | 2/1968 | Allsop |
| 3,498,174 A | 3/1970 | Schuster et al. |
| 3,584,667 A | 6/1971 | Reiland |
| 3,640,416 A | 2/1972 | Temple |
| 3,812,757 A | 5/1974 | Reiland |

(Continued)

FOREIGN PATENT DOCUMENTS

DE             3630863            3/1988

(Continued)

OTHER PUBLICATIONS

*EBI Omega 21* Brochure, EBI Spine Systems, pub. 1999.

(Continued)

*Primary Examiner* — Eduardo C Robert
*Assistant Examiner* — David Comstock
(74) *Attorney, Agent, or Firm* — John C. McMahon

(57) ABSTRACT

A polyaxial bone screw includes a head member and a shank member. The shank has a capture end and an opposite threaded end for threaded insertion into a vertebra. The head has a U-shaped cradle for receiving a spinal fixation rod and a central bore for receiving the capture end of the shank. An expandible retainer ring with a radial split is snapped onto the capture end of the shank to retain it within the head. The retainer ring has a spherical outer surface which forms a ball joint with a spherical socket cavity within the head to enable the head to be angled relative to the shank. A threaded closure plug is tightened within the cradle to clamp the rod into engagement with a knurled dome on the capture end of the shank to secure the rod relative to the vertebra.

26 Claims, 7 Drawing Sheets

U.S. PATENT DOCUMENTS

| | | |
|---|---|---|
| 3,963,322 A | 6/1976 | Cryctko |
| 4,033,139 A | 7/1977 | Frederick |
| 4,103,422 A | 8/1978 | Weiss |
| 4,269,246 A | 5/1981 | Larson et al. |
| 4,373,754 A | 2/1983 | Bollfrass et al. |
| 4,492,500 A | 1/1985 | Ewing |
| 4,506,917 A | 3/1985 | Arne |
| 4,577,448 A | 3/1986 | Howorth |
| 4,600,224 A | 7/1986 | Blose |
| 4,641,636 A | 2/1987 | Cotrel |
| 4,703,954 A | 11/1987 | Ortloff et al. |
| 4,707,001 A | 11/1987 | Johnson |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,838,264 A | 6/1989 | Bremer et al. |
| 4,850,775 A | 7/1989 | Lee |
| 4,946,458 A | 8/1990 | Harms et al. |
| 5,005,562 A | 4/1991 | Cotrel |
| 5,019,080 A | 5/1991 | Hemer |
| 5,022,791 A | 6/1991 | Isler |
| 5,026,373 A | 6/1991 | Ray et al. |
| 5,056,492 A | 10/1991 | Banse |
| 5,067,955 A | 11/1991 | Cotrel |
| 5,073,074 A | 12/1991 | Corrigan et al. |
| 5,092,635 A | 3/1992 | DeLange et al. |
| 5,129,388 A | 7/1992 | Vignaud et al. |
| 5,147,360 A | 9/1992 | Dubousset |
| 5,154,719 A | 10/1992 | Cotrel |
| 5,176,483 A | 1/1993 | Baumann et al. |
| 5,207,678 A | 5/1993 | Harms et al. |
| 5,217,497 A | 6/1993 | Mehdian |
| 5,261,907 A | 11/1993 | Vignaud et al. |
| 5,261,912 A | 11/1993 | Frigg |
| 5,275,601 A | 1/1994 | Gogolewski et al. |
| 5,282,707 A | 2/1994 | Palm |
| 5,312,404 A | 5/1994 | Asher et al. |
| 5,321,901 A | 6/1994 | Kelly |
| 5,334,203 A | 8/1994 | Wagner |
| 5,346,493 A | 9/1994 | Stahurski et al. |
| 5,354,299 A | 10/1994 | Coleman |
| 5,358,289 A | 10/1994 | Banker et al. |
| 5,360,431 A | 11/1994 | Puno |
| 5,364,400 A | 11/1994 | Rego, Jr. et al. |
| 5,382,248 A | 1/1995 | Jacobson et al. |
| 5,385,583 A | 1/1995 | Cotrel |
| 5,387,212 A | 2/1995 | Yuan et al. |
| 5,395,371 A | 3/1995 | Miller et al. |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,487,742 A | 1/1996 | Cotrel |
| 5,496,321 A | 3/1996 | Puno et al. |
| 5,499,892 A | 3/1996 | Reed |
| 5,507,747 A | 4/1996 | Yuan et al. |
| 5,545,165 A | 8/1996 | Biedermann et al. |
| 5,554,157 A | 9/1996 | Errico et al. |
| 5,562,663 A | 10/1996 | Wisnewski et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,591,235 A | 1/1997 | Kuslich |
| 5,601,553 A | 2/1997 | Trebing et al. |
| 5,607,304 A | 3/1997 | Bailey et al. |
| 5,607,426 A | 3/1997 | Ralph et al. |
| 5,624,442 A | 4/1997 | Mellinger et al. |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,713,705 A | 2/1998 | Grunbichler |
| 5,713,898 A | 2/1998 | Stucker et al. |
| 5,716,356 A | 2/1998 | Biedermann et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof |
| 5,938,663 A | 8/1999 | Petreto |
| 5,944,465 A | 8/1999 | Janitzki |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A * | 1/2000 | Richelsoph et al. ............ 606/61 |
| 6,019,759 A | 2/2000 | Rogozinski |
| 6,022,350 A | 2/2000 | Ganem |
| 6,053,078 A | 4/2000 | Parker |
| 6,053,917 A | 4/2000 | Sherman et al. |
| 6,056,753 A | 5/2000 | Jackson |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,139,550 A | 10/2000 | Michelson |
| 6,143,032 A | 11/2000 | Schafer et al. |
| 6,146,383 A | 11/2000 | Studer et al. |
| 6,149,533 A | 11/2000 | Finn |
| 6,183,472 B1 | 2/2001 | Lutz |
| 6,186,718 B1 | 2/2001 | Fogard |
| 6,187,005 B1 | 2/2001 | Brace et al. |
| 6,193,719 B1 | 2/2001 | Gournay et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,248,105 B1 | 6/2001 | Schlapfer et al. |
| 6,254,146 B1 | 7/2001 | Church |
| 6,254,602 B1 | 7/2001 | Justis |
| 6,261,039 B1 | 7/2001 | Reed |
| 6,273,888 B1 | 8/2001 | Justis |
| 6,280,442 B1 | 8/2001 | Barker et al. |

| Patent | Date | Inventor |
|---|---|---|
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 * | 10/2001 | Morrison et al. ............... 606/61 |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| 6,331,179 B1 | 12/2001 | Freid et al. |
| 6,349,794 B2 | 2/2002 | Spencer |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 * | 4/2002 | Amrein et al. ............... 606/61 |
| 6,402,752 B2 | 6/2002 | Schaffler-Wachter et al. |
| 6,440,135 B2 | 8/2002 | Orgay et al. |
| 6,440,137 B1 | 8/2002 | Horvath et al. |
| 6,443,953 B1 | 9/2002 | Perra et al. |
| 6,451,021 B1 | 9/2002 | Ralph et al. |
| 6,454,772 B1 | 9/2002 | Jackson |
| 6,471,703 B1 | 10/2002 | Ashman |
| 6,471,705 B1 | 10/2002 | Biedermann et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,520,963 B1 | 2/2003 | McKinley |
| 6,527,804 B1 | 3/2003 | Gauchet et al. |
| 6,530,929 B1 | 3/2003 | Jusis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,602,255 B1 | 8/2003 | Campbell |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,526 B1 | 11/2003 | Arafiles |
| 6,656,179 B1 | 12/2003 | Schaefer et al. |
| 6,656,181 B2 | 12/2003 | Dixon et al. |
| 6,660,004 B2 * | 12/2003 | Barker et al. ............... 606/61 |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,677 B1 | 5/2005 | Lin |
| 791,548 A1 | 6/2005 | Fischer |
| 6,932,817 B2 | 8/2005 | Baynham et al. |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,426 B2 | 10/2006 | Moumene et al. |
| 7,128,743 B2 | 10/2006 | Metz-Stavenhagen |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,445,627 B2 | 11/2008 | Hawkes et al. |
| 7,476,228 B2 | 1/2009 | Abdou |
| 7,479,156 B2 | 1/2009 | Lourdel et al. |
| 7,491,218 B2 | 2/2009 | Landry et al. |
| 7,491,221 B2 | 2/2009 | David |
| 7,503,918 B2 | 3/2009 | Baccelli et al. |

| Patent No. | Date | Inventor |
|---|---|---|
| 7,503,924 B2 | 3/2009 | Lee et al. |
| 7,524,323 B2 | 4/2009 | Malandain |
| 7,527,640 B2 | 5/2009 | Ziolo et al. |
| 7,530,992 B2 | 5/2009 | Biedermann et al. |
| 7,559,943 B2 | 7/2009 | Mjuwid |
| 7,563,264 B2 | 7/2009 | Landry et al. |
| 7,563,275 B2 | 7/2009 | Falahee et al. |
| 7,569,061 B2 | 8/2009 | Colleran |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,604,656 B2 | 10/2009 | Shluzas |
| 7,611,518 B2 | 11/2009 | Walder et al. |
| 7,615,068 B2 | 11/2009 | Timm et al. |
| 7,621,941 B2 | 11/2009 | Schlapfer et al. |
| 7,625,394 B2 | 12/2009 | Molz, IV et al. |
| 7,641,674 B2 | 1/2010 | Young |
| 7,645,294 B2 | 1/2010 | Kalfasetd |
| 7,648,522 B2 | 1/2010 | David |
| 2001/0001119 A1 | 5/2001 | Lombardo |
| 2002/0026193 A1 | 2/2002 | Barker et al. |
| 2002/0035366 A1 | 3/2002 | Walder et al. |
| 2002/0045898 A1 | 4/2002 | Freid et al. |
| 2002/0072751 A1* | 6/2002 | Jackson .......... 606/73 |
| 2002/0082602 A1 | 6/2002 | Biedermann et al. |
| 2002/0111626 A1 | 8/2002 | Ralph et al. |
| 2002/0133154 A1 | 9/2002 | Saint Martin |
| 2002/0133159 A1* | 9/2002 | Jackson .......... 606/73 |
| 2002/0203511 | 9/2002 | Wilson-MacDonald et al. |
| 2002/0143341 A1 | 10/2002 | Biedermann |
| 2002/0173789 A1 | 11/2002 | Howland |
| 2002/0193795 A1 | 12/2002 | Gertzbein et al. |
| 2003/0023240 A1* | 1/2003 | Amrein et al. .......... 606/61 |
| 2003/0023243 A1 | 1/2003 | Biedermann et al. |
| 2003/0028191 A1 | 2/2003 | Shluzas |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0153068 A1 | 8/2004 | Janowski |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172032 A1 | 9/2004 | Jackson |
| 2004/0176766 A1 | 9/2004 | Shluzas |
| 2004/0186473 A1 | 9/2004 | Cournoyer et al. |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0049589 A1 | 3/2005 | Jackson |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0096653 A1 | 5/2005 | Doubler |
| 2005/0096654 A1 | 5/2005 | Lin |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203516 A1 | 9/2005 | Biedermann et al. |
| 2005/0216003 A1 | 9/2005 | Biedermann et al. |
| 2005/0228379 A1 | 10/2005 | Jackson |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0260058 A1 | 11/2005 | Cassagne, III |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Liebermann |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079899 A1 | 4/2006 | Ritland |
| 2006/0084981 A1 | 4/2006 | Shluzas |
| 2006/0084989 A1 | 4/2006 | Dickinson et al. |
| 2006/0084993 A1 | 4/2006 | Landry et al. |
| 2006/0084995 A1 | 4/2006 | Biedermann et al. |
| 2006/0089643 A1 | 4/2006 | Mujwid |
| 2006/0089644 A1 | 4/2006 | Felix |
| 2006/0095037 A1 | 5/2006 | Jones et al. |
| 2006/0100621 A1 | 5/2006 | Jackson |
| 2006/0106380 A1 | 5/2006 | Colleran et al. |
| 2006/0106383 A1 | 5/2006 | Biedermann et al. |
| 2006/0116677 A1 | 6/2006 | Burd et al. |
| 2006/0129147 A1 | 6/2006 | Biedermann et al. |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |

| | | | | | | |
|---|---|---|---|---|---|---|
| 2006/0166535 A1 | 7/2006 | Brumfield et al. | | 2007/0198014 A1 | 8/2007 | Graf et al. |
| 2006/0167455 A1 | 7/2006 | Clement et al. | | 2007/0208344 A1 | 9/2007 | Young |
| 2006/0173454 A1 | 8/2006 | Spitler et al. | | 2007/0225707 A1 | 9/2007 | Wisnewski et al. |
| 2006/0173456 A1 | 8/2006 | Hawkes et al. | | 2007/0225711 A1 | 9/2007 | Ensign |
| 2006/0195098 A1 | 8/2006 | Schumacher | | 2007/0233078 A1 | 10/2007 | Justis et al. |
| 2006/0200128 A1 | 9/2006 | Mueller | | 2007/0233080 A1 | 10/2007 | Na et al. |
| 2006/0200131 A1 | 9/2006 | Chao et al. | | 2007/0233086 A1 | 10/2007 | Harms et al. |
| 2006/0200149 A1 | 9/2006 | Hoy et al. | | 2007/0233087 A1 | 10/2007 | Schlapfer |
| 2006/0212034 A1 | 9/2006 | Triplett et al. | | 2007/0250061 A1 | 10/2007 | Chin et al. |
| 2006/0217716 A1 | 9/2006 | Baker et al. | | 2007/0260243 A1 | 11/2007 | Biedermann |
| 2006/0229614 A1 | 10/2006 | Foley et al. | | 2007/0270806 A1 | 11/2007 | Foley et al. |
| 2006/0229615 A1 | 10/2006 | Abdou | | 2007/0270807 A1 | 11/2007 | Armstrong et al. |
| 2006/0235389 A1 | 10/2006 | Albert et al. | | 2007/0270810 A1 | 11/2007 | Sanders |
| 2006/0235392 A1 | 10/2006 | Hammer et al. | | 2007/0270813 A1 | 11/2007 | Garamszegi |
| 2006/0235393 A1 | 10/2006 | Bono et al. | | 2007/0270815 A1 | 11/2007 | Johnson et al. |
| 2006/0241593 A1 | 10/2006 | Sherman et al. | | 2007/0270830 A1 | 11/2007 | Morrison |
| 2006/0241595 A1 | 10/2006 | Molz, IV et al. | | 2007/0270831 A1 | 11/2007 | Dewey et al. |
| 2006/0241599 A1 | 10/2006 | Konieczynski et al. | | 2007/0270832 A1 | 11/2007 | Moore |
| 2006/0241600 A1 | 10/2006 | Ensign et al. | | 2007/0270835 A1 | 11/2007 | Wisnewski |
| 2006/0247624 A1 | 11/2006 | Banouskou et al. | | 2007/0270839 A1 | 11/2007 | Jeon et al. |
| 2006/0247631 A1 | 11/2006 | Ahn et al. | | 2007/0288004 A1 | 12/2007 | Alvarez |
| 2006/0247636 A1 | 11/2006 | Yuan et al. | | 2008/0009862 A1 | 1/2008 | Hoffman |
| 2006/0247779 A1 | 11/2006 | Gordon et al. | | 2008/0009864 A1 | 1/2008 | Forton et al. |
| 2006/0264933 A1 | 11/2006 | Baker et al. | | 2008/0015578 A1 | 1/2008 | Erickson et al. |
| 2006/0264936 A1 | 11/2006 | Partin et al. | | 2008/0015579 A1 | 1/2008 | Whipple |
| 2006/0276787 A1 | 12/2006 | Zubok et al. | | 2008/0015580 A1 | 1/2008 | Chao |
| 2006/0276789 A1 | 12/2006 | Jackson | | 2008/0015584 A1 | 1/2008 | Richelsoph |
| 2006/0276791 A1 | 12/2006 | Shluzas | | 2008/0015586 A1 | 1/2008 | Krishna et al. |
| 2006/0276792 A1 | 12/2006 | Ensign et al. | | 2008/0021454 A1 | 1/2008 | Chao et al. |
| 2006/0282074 A1 | 12/2006 | Renaud et al. | | 2008/0021455 A1 | 1/2008 | Chao et al. |
| 2006/0293659 A1 | 12/2006 | Alvarez | | 2008/0021462 A1 | 1/2008 | Trieu |
| 2006/0293665 A1 | 12/2006 | Shluzas | | 2008/0021464 A1 | 1/2008 | Morin et al. |
| 2006/0293666 A1 | 12/2006 | Matthis et al. | | 2008/0021473 A1 | 1/2008 | Butler et al. |
| 2007/0016188 A1 | 1/2007 | Boehm, Jr. et al. | | 2008/0027432 A1 | 1/2008 | Strauss et al. |
| 2007/0016198 A1 | 1/2007 | Boehm, Jr. et al. | | 2008/0039838 A1 | 2/2008 | Landry et al. |
| 2007/0021750 A1 | 1/2007 | Shluzas et al. | | 2008/0039843 A1 | 2/2008 | Abdou |
| 2007/0043355 A1 | 2/2007 | Bette et al. | | 2008/0045951 A1 | 2/2008 | Fanger et al. |
| 2007/0043357 A1 | 2/2007 | Kirschman | | 2008/0045955 A1 | 2/2008 | Berrevoets et al. |
| 2007/0043358 A1 | 2/2007 | Molz, IV et al. | | 2008/0045957 A1 | 2/2008 | Landry et al. |
| 2007/0043359 A1 | 2/2007 | Altarac et al. | | 2008/0051780 A1 | 2/2008 | Vaidya et al. |
| 2007/0043364 A1 | 2/2007 | Cawley et al. | | 2008/0058811 A1 | 3/2008 | Alleyne et al. |
| 2007/0049933 A1 | 3/2007 | Ahn et al. | | 2008/0058812 A1 | 3/2008 | Zehnder |
| 2007/0055235 A1 | 3/2007 | Janowski et al. | | 2008/0065073 A1 | 3/2008 | Perriello et al. |
| 2007/0055238 A1 | 3/2007 | Biedermann et al. | | 2008/0065075 A1 | 3/2008 | Dant |
| 2007/0055239 A1 | 3/2007 | Sweeney et al. | | 2008/0065077 A1 | 3/2008 | Ferree |
| 2007/0055240 A1 | 3/2007 | Matthis et al. | | 2008/0071273 A1 | 3/2008 | Hawkes et al. |
| 2007/0055241 A1 | 3/2007 | Matthis et al. | | 2008/0071274 A1 | 3/2008 | Ensign |
| 2007/0055242 A1 | 3/2007 | Bailly | | 2008/0071277 A1 | 3/2008 | Warnick |
| 2007/0055244 A1 | 3/2007 | Jackson | | 2008/0077139 A1 | 3/2008 | Landry et al. |
| 2007/0073291 A1 | 3/2007 | Cordaro et al. | | 2008/0086131 A1 | 4/2008 | Daly et al. |
| 2007/0078460 A1 | 4/2007 | Frigg et al. | | 2008/0086132 A1 | 4/2008 | Biedermann et al. |
| 2007/0083199 A1 | 4/2007 | Baccelli | | 2008/0097441 A1 | 4/2008 | Hayes et al. |
| 2007/0088357 A1 | 4/2007 | Johnson et al. | | 2008/0097457 A1 | 4/2008 | Warnick |
| 2007/0093817 A1 | 4/2007 | Barrus et al. | | 2008/0108992 A1 | 5/2008 | Barry et al. |
| 2007/0093818 A1 | 4/2007 | Biedermann et al. | | 2008/0119858 A1 | 5/2008 | Potash |
| 2007/0093819 A1 | 4/2007 | Albert | | 2008/0140075 A1 | 6/2008 | Ensign et al. |
| 2007/0093826 A1 | 4/2007 | Hawkes et al. | | 2008/0161859 A1 | 7/2008 | Nilsson |
| 2007/0093827 A1 | 4/2007 | Warnick | | 2008/0161863 A1 | 7/2008 | Arnold et al. |
| 2007/0093831 A1 | 4/2007 | Abdelgany et al. | | 2008/0177321 A1 | 7/2008 | Drewry et al. |
| 2007/0100341 A1 | 5/2007 | Reglos et al. | | 2008/0177322 A1 | 7/2008 | Davis et al. |
| 2007/0118117 A1 | 5/2007 | Altarac et al. | | 2008/0177332 A1 | 7/2008 | Reiley et al. |
| 2007/0118118 A1 | 5/2007 | Kwak et al. | | 2008/0183215 A1 | 7/2008 | Altarac et al. |
| 2007/0118123 A1 | 5/2007 | Strausbaugh et al. | | 2008/0183223 A1 | 7/2008 | Jeon et al. |
| 2007/0118124 A1 | 5/2007 | Biedermann et al. | | 2008/0195159 A1 | 8/2008 | Kloss et al. |
| 2007/0123862 A1 | 5/2007 | Warnick | | 2008/0200956 A1 | 8/2008 | Beckwith et al. |
| 2007/0123864 A1 | 5/2007 | Walder et al. | | 2008/0215095 A1 | 9/2008 | Biedermann et al. |
| 2007/0123867 A1 | 5/2007 | Kirschman | | 2008/0228229 A1 | 9/2008 | Walder et al. |
| 2007/0123870 A1 | 5/2007 | Jeon et al. | | 2008/0234734 A1 | 9/2008 | Walder et al. |
| 2007/0161986 A1 | 7/2007 | Levy | | 2008/0234756 A1 | 9/2008 | Sutcliffe et al. |
| 2007/0161994 A1 | 7/2007 | Lowery et al. | | 2008/0234759 A1 | 9/2008 | Marino |
| 2007/0161995 A1 | 7/2007 | Trautwein et al. | | 2008/0249570 A1 | 10/2008 | Carson et al. |
| 2007/0161996 A1 | 7/2007 | Biedermann et al. | | 2008/0262548 A1 | 10/2008 | Lange et al. |
| 2007/0161999 A1 | 7/2007 | Biedermann et al. | | 2008/0262556 A1 | 10/2008 | Jacofsky et al. |
| 2007/0167948 A1 | 7/2007 | Abdou | | 2008/0269742 A1 | 10/2008 | Levy et al. |
| 2007/0167949 A1 | 7/2007 | Altarac et al. | | 2008/0269809 A1 | 10/2008 | Garamszegi |
| 2007/0173819 A1 | 7/2007 | Sandlin | | 2008/0287994 A1 | 11/2008 | Perez-Cruet et al. |
| 2007/0173820 A1 | 7/2007 | Trieu | | 2008/0288002 A1 | 11/2008 | Crall et al. |
| 2007/0173828 A1 | 7/2007 | Firkins et al. | | 2008/0306528 A1 | 12/2008 | Winslow et al. |
| 2007/0191839 A1 | 8/2007 | Justis et al. | | 2008/0306533 A1 | 12/2008 | Winslow et al. |

| | | | | | |
|---|---|---|---|---|---|
| 2008/0306539 A1 | 12/2008 | Cain et al. | DE | 4425392 | 11/1995 |
| 2008/0312655 A1 | 12/2008 | Kirschman et al. | DE | 19507141 A1 | 9/1996 |
| 2008/0312692 A1 | 12/2008 | Brennan et al. | DE | 19509331 | 9/1996 |
| 2008/0312696 A1 | 12/2008 | Butters et al. | DE | 28910798 | 12/1999 |
| 2008/0312701 A1 | 12/2008 | Butters et al. | DE | 19951145 | 5/2001 |
| 2009/0005787 A1 | 1/2009 | Crall et al. | DE | 10157969 | 2/2003 |
| 2009/0005813 A1 | 1/2009 | Crall et al. | EP | 195455 | 9/1986 |
| 2009/0005814 A1 | 1/2009 | Miller et al. | EP | 172130 | 2/1987 |
| 2009/0012567 A1 | 1/2009 | Biedermann et al. | EP | 276153 | 7/1988 |
| 2009/0018591 A1 | 1/2009 | Hawkes et al. | EP | 0276153 | 7/1988 |
| 2009/0024169 A1 | 1/2009 | Triplett et al. | EP | 465158 | 1/1992 |
| 2009/0030457 A1 | 1/2009 | Janowski et al. | EP | 0885598 | 12/1998 |
| 2009/0036929 A1 | 2/2009 | Reglos et al. | EP | 1090595 | 4/2001 |
| 2009/0036932 A1 | 2/2009 | Rouyer et al. | EP | 1121902 A2 | 8/2001 |
| 2009/0036934 A1 | 2/2009 | Biedermann et al. | EP | 1190678 | 3/2002 |
| 2009/0062860 A1 | 3/2009 | Frasier et al. | EP | 1210914 | 6/2002 |
| 2009/0062865 A1 | 3/2009 | Schumacher | EP | 1277444 | 1/2003 |
| 2009/0062867 A1 | 3/2009 | Schumacher | EP | 1449486 | 8/2004 |
| 2009/0062914 A1 | 3/2009 | Marino | EP | 1570795 | 9/2005 |
| 2009/0069849 A1 | 3/2009 | Oh et al. | EP | 1579816 | 9/2005 |
| 2009/0069852 A1 | 3/2009 | Farris et al. | EP | 1634537 | 3/2006 |
| 2009/0069853 A1 | 3/2009 | Schumacher | EP | 1925263 | 5/2008 |
| 2009/0076550 A1 | 3/2009 | Bernhardt, Jr. et al. | FR | 2467312 | 4/1981 |
| 2009/0076552 A1 | 3/2009 | Tornier | FR | 2729291 | 7/1996 |
| 2009/0082809 A1 | 3/2009 | Nguyen et al. | FR | 2796545 | 1/2001 |
| 2009/0082812 A1 | 3/2009 | Lewis | FR | 2856578 | 6/2003 |
| 2009/0082815 A1 | 3/2009 | Zylber et al. | FR | 2865373 | 1/2004 |
| 2009/0082819 A1 | 3/2009 | Blain et al. | FR | 2865375 | 1/2004 |
| 2009/0088799 A1 | 4/2009 | Yeh | FR | 2865377 | 1/2004 |
| 2009/0088807 A1 | 4/2009 | Castaneda et al. | FR | 2857850 | 4/2004 |
| 2009/0093843 A1 | 4/2009 | Lemoine et al. | FR | 2865378 | 10/2004 |
| 2009/0105769 A1 | 4/2009 | Rock et al. | FR | 2925288 | 6/2009 |
| 2009/0105770 A1 | 4/2009 | Berrevoets et al. | GB | 203508 | 9/1923 |
| 2009/0105771 A1 | 4/2009 | Lei et al. | GB | 2082709 | 3/1982 |
| 2009/0118772 A1 | 5/2009 | Diederich et al. | GB | 2140523 | 11/1984 |
| 2009/0131983 A1 | 5/2009 | Biedermann | GB | 2365345 | 2/2002 |
| 2009/0138044 A1 | 5/2009 | Bergeron et al. | JP | 9-504727 | 5/1997 |
| 2009/0138052 A1 | 5/2009 | Biedermann et al. | SU | 371359 | 8/1973 |
| 2009/0143827 A1 | 6/2009 | Levy et al. | SU | 371359 | 2/1993 |
| 2009/0143829 A1 | 6/2009 | Shluzas | WO | WO92/03100 | 3/1992 |
| 2009/0149887 A1 | 6/2009 | Schlaepfer et al. | WO | WO94/10927 | 5/1994 |
| 2009/0163955 A1 | 6/2009 | Moumene et al. | WO | WO94/10944 | 5/1994 |
| 2009/0163956 A1 | 6/2009 | Biedermann et al. | WO | WO94/26191 | 11/1994 |
| 2009/0163961 A1 | 6/2009 | Kirschman | WO | WO95/01132 | 1/1995 |
| 2009/0163963 A1 | 6/2009 | Berrevoets | WO | WO95/35067 | 12/1995 |
| 2009/0182380 A1 | 7/2009 | Abdelgany | WO | WO96/06576 | 3/1996 |
| 2009/0192548 A1 | 7/2009 | Jeon et al. | WO | WO96/28118 | 9/1996 |
| 2009/0192551 A1 | 7/2009 | Cianfrani et al. | WO | WO97/14366 | 4/1997 |
| 2009/0198280 A1 | 8/2009 | Spratt et al. | WO | WO98/32386 | 7/1998 |
| 2009/0198289 A1 | 8/2009 | Manderson | WO | WO01/49191 | 7/2001 |
| 2009/0198291 A1 | 8/2009 | Kevin et al. | WO | WO02/054966 | 7/2002 |
| 2009/0204155 A1 | 8/2009 | Aschmann | WO | WO03/068088 | 8/2003 |
| 2009/0216280 A1 | 8/2009 | Hutchinson | WO | WO2004/021900 | 3/2004 |
| 2009/0248030 A1 | 10/2009 | Butler et al. | WO | WO2004/041100 | 5/2004 |
| 2009/0248075 A1 | 10/2009 | Ogilvie et al. | WO | WO2004/089245 | 10/2004 |
| 2009/0248088 A1 | 10/2009 | Biedermann | WO | WO2004/107997 | 12/2004 |
| 2009/0254125 A1 | 10/2009 | Predick | WO | WO2005/000136 | 1/2005 |
| 2009/0259254 A1 | 10/2009 | Pisharodi | WO | WO2005/000137 | 1/2005 |
| 2009/0264896 A1 | 10/2009 | Biedermann et al. | WO | WO2005/020829 | 3/2005 |
| 2009/0264933 A1 | 10/2009 | Carls et al. | WO | WO2005/072632 | 8/2005 |
| 2009/0270916 A1 | 10/2009 | Ramsay et al. | WO | WO2005/082262 | 9/2005 |
| 2009/0270917 A1 | 10/2009 | Boehm | WO | WO2005/099400 | 10/2005 |
| 2009/0281571 A1 | 11/2009 | Weaver et al. | WO | WO2006/005198 | 1/2006 |
| 2009/0281572 A1 | 11/2009 | White | WO | WO2006/012088 | 2/2006 |
| 2009/0281573 A1 | 11/2009 | Biedermann et al. | WO | WO2006/017616 | 2/2006 |
| 2009/0287253 A1 | 11/2009 | Felix et al. | WO | WO2006/028537 | 3/2006 |
| 2009/0299415 A1 | 12/2009 | Pimenta | WO | WO2006/119241 | 11/2006 |
| 2009/0306719 A1 | 12/2009 | Meyer, III et al. | WO | WO2007/118045 | 10/2007 |
| 2009/0306720 A1 | 12/2009 | Doubler et al. | WO | WO2007/124222 | 11/2007 |
| 2009/0312804 A1 | 12/2009 | Gamache et al. | WO | WO2007/130835 | 11/2007 |
| 2009/0326582 A1 | 12/2009 | Songer et al. | WO | WO2007/130840 | 11/2007 |
| 2009/0326587 A1 | 12/2009 | Matthis et al. | WO | WO2007/130941 | 11/2007 |
| 2010/0004692 A1 | 1/2010 | Biedermann et al. | WO | WO2008/088731 | 7/2008 |
| 2010/0010540 A1 | 1/2010 | Park | WO | WO2009/015100 | 1/2009 |
| 2010/0016898 A1 | 1/2010 | Shluzas | | | |

FOREIGN PATENT DOCUMENTS

| | | |
|---|---|---|
| DE | 373809 | 5/1989 |
| DE | 9202745.8 | 4/1992 |

OTHER PUBLICATIONS

*Claris Instrumentation* Brochure, G Med, pub. 1997.
*VLS System Variable Locking Screw* Brochure, Interpore Cross International, 1999.

*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*SDRS Surgical Dynamics Rod System* Brochure, Surgical Dynamics, pub. 1998-1999.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.
Brochure of Tyco/Healthcare/Surgical Dynamics on Spiral Radius 90D, Publication Date: Sep. 2001, pp. 1-8.
Spine, Lipcott, Williams & Wilkins, Inc. vol. 24, No. 15, p. 1495 Aug. 1999.

\* cited by examiner

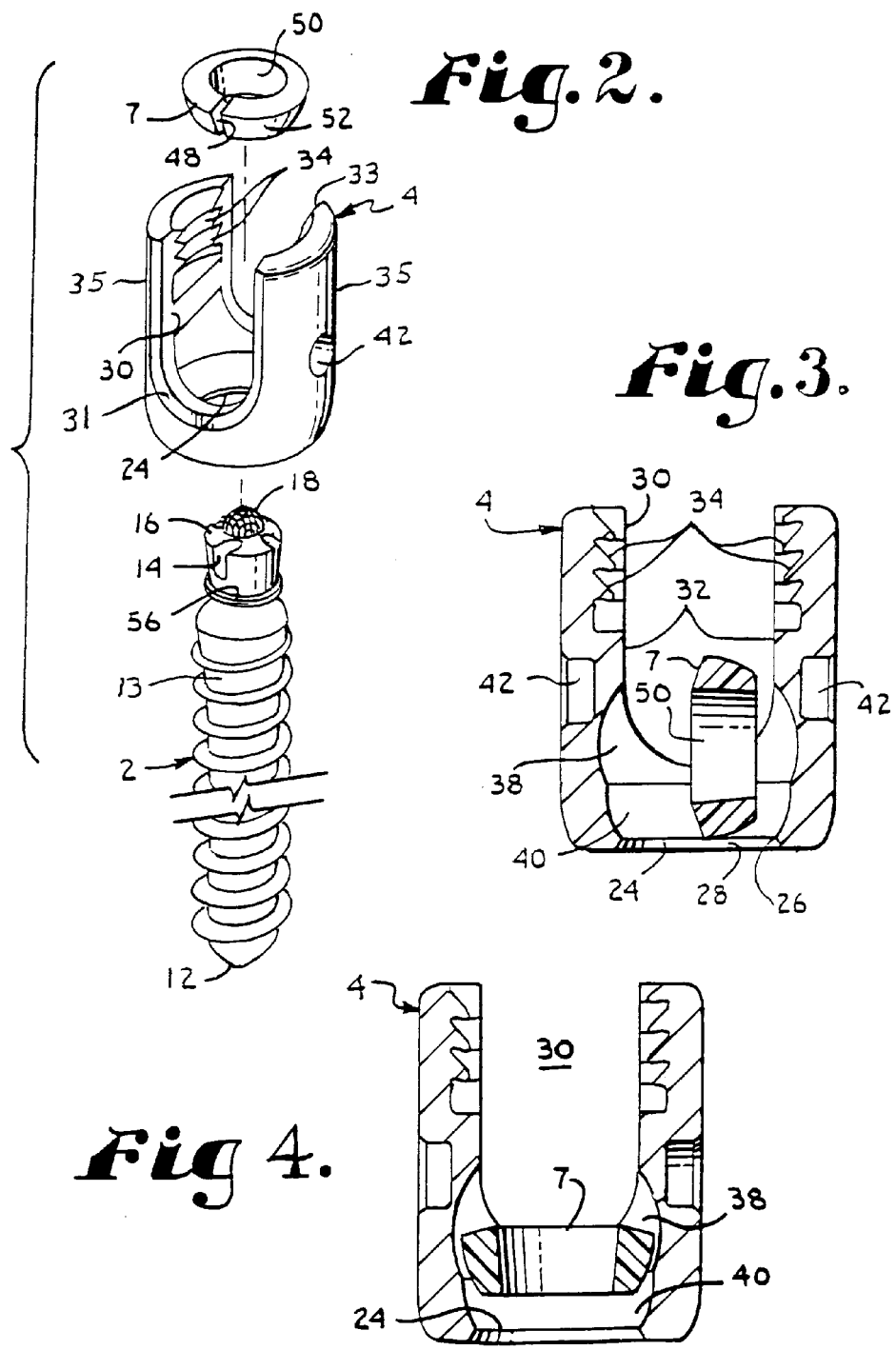

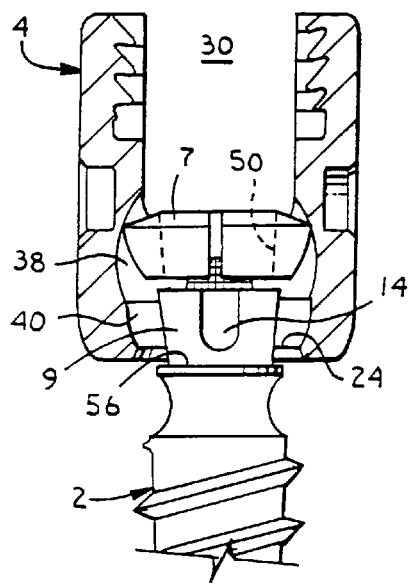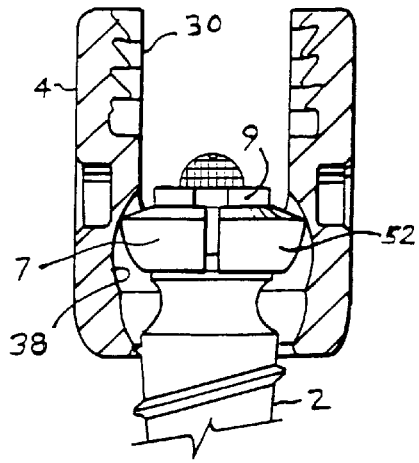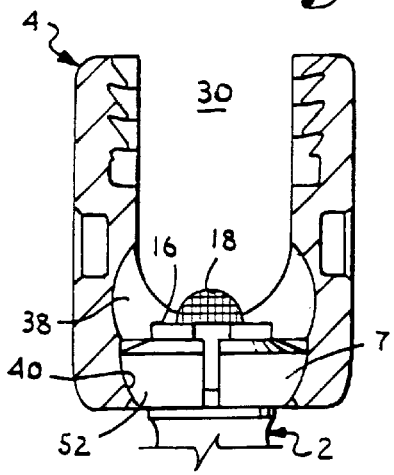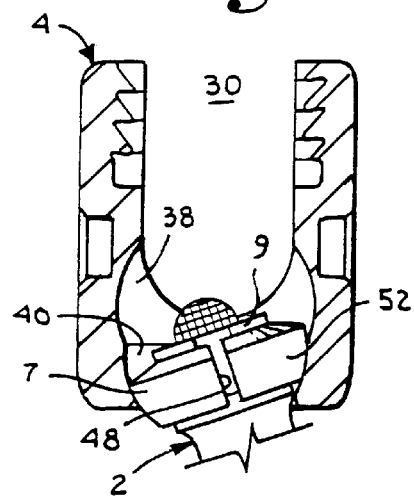

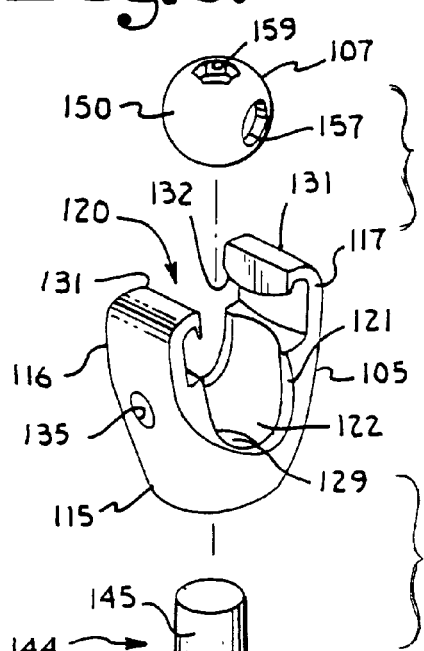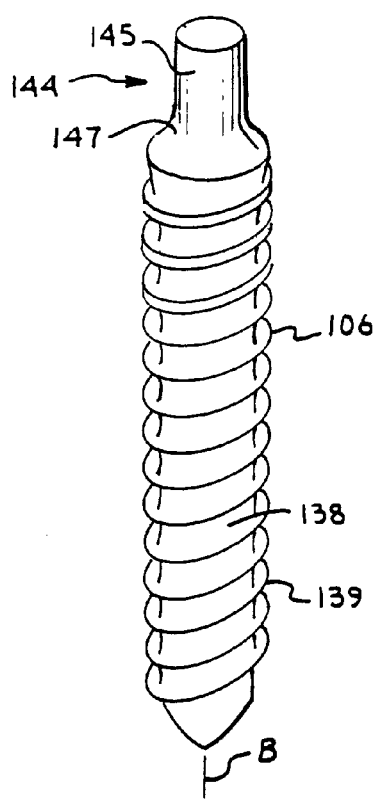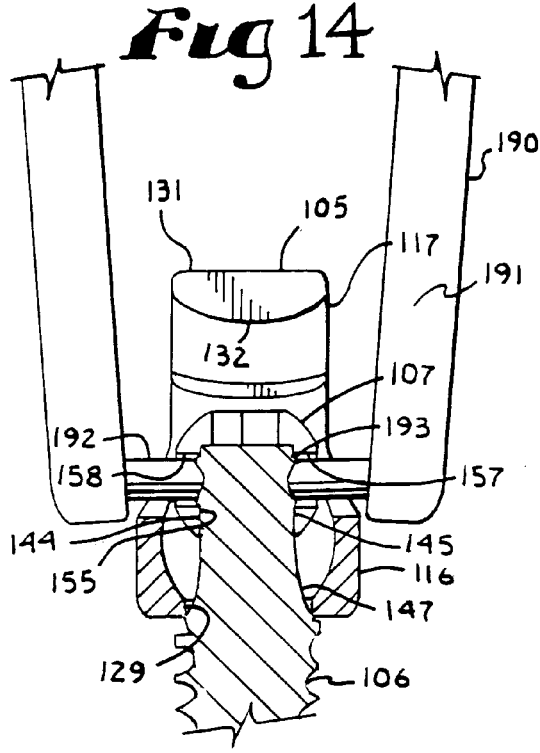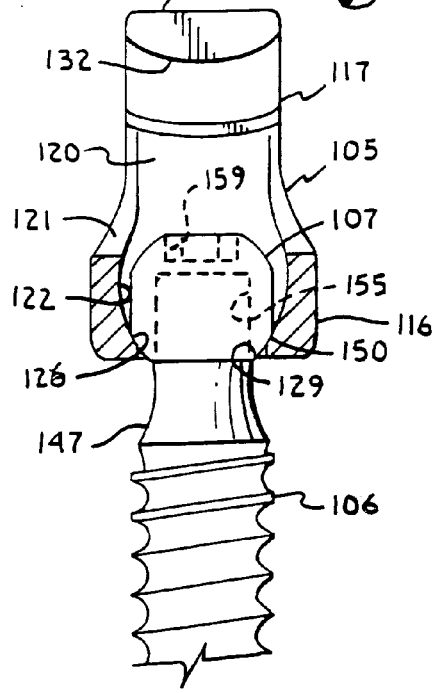

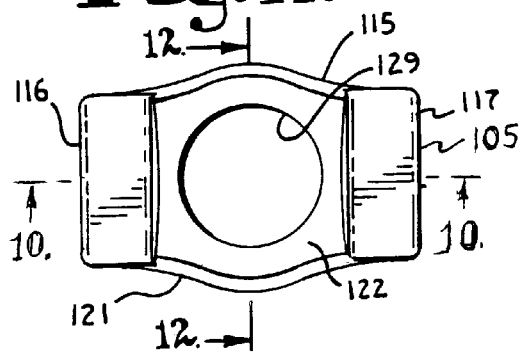
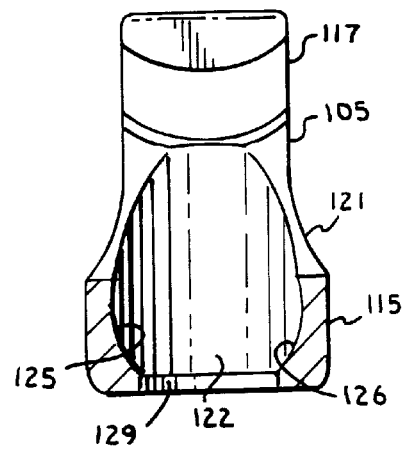
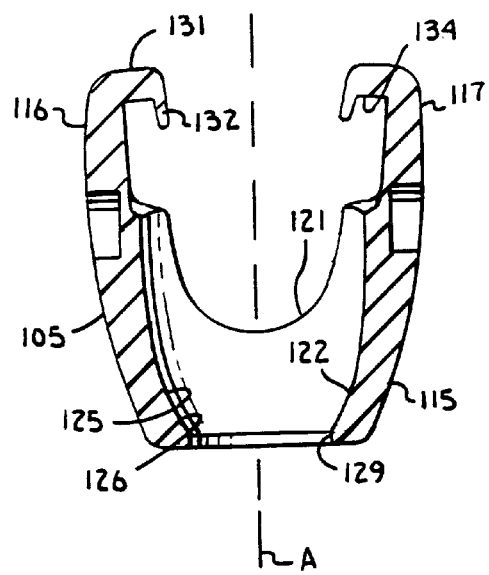
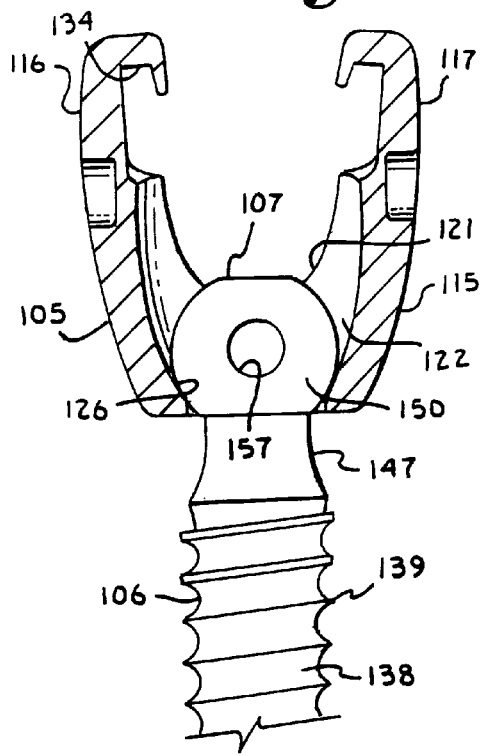

POLYAXIAL BONE SCREW APPARATUS

BACKGROUND OF THE INVENTION

The present invention is directed to a bone screw of the type wherein a head of the bone screw is swingable or can swivel about the shank of the bone screw until the surgeon is satisfied with the relative placement of the two parts and thereafter the head can be locked in position relative to the shank. Such screws are also referred to as polyaxial head or swivel head bone screws, since the head can be positioned in any of a number of angular configurations relative to the shank.

Bone screws are advantageously utilized in many types of spinal surgery in order to secure various implants to vertebrae along the spinal column. Bone screws of this type typically have a shank that is threaded and adapted to be implanted into a vertebral body of a vertebra. The bone screw includes a head which is designed to extend beyond the vertebra and which has a channel to receive another implant. Typically the channel will receive a rod or a rod-like member. In bone screws of this type, the head may be open, in which case a closure must be used to close between opposite sides of the head once a rod-like implant is placed therein, or closed wherein a rod-like implant passes through the head of a bone screw. Open head screws are most often used, mainly because it is difficult to feed long rods through closed head screws.

Bone screws are also available with heads permanently fixed relative to a shank or with polyaxial heads that initially swivel to allow placement and are then lockable in a desired positional configuration. When the head and shank of the bone screw are fixed in position relative to each other, it is not always possible to insert a bone screw into the bone in such a manner that the head will be in the best position for receiving other implants. Consequently, the polyaxial head bone screws have been designed that allow the head of the bone screw to rotate or swivel about an upper end of the shank of the bone screw, while the surgeon is positioning other implants and finding the best position for the bone screw head. However, once the surgeon has determined that the head is in the best position, it is then necessary to lock or fix the head relative to the shank. Different types of structures have been previously developed for this purpose. Unfortunately, the prior art devices have a tendency to be bulky, slip under high loading or require many parts.

It is desirable to have a polyaxial head bone screw that can be captured by the shank prior to locking of the head, but that allows the head to freely swivel or pivot about a top of the shank prior to locking. It is then further desirable to have the head capable of being fixably locked in a configuration or position relative to the shank where the head best fits with other elements of the overall spinal implant.

As noted above, many prior art swivel type bone screws have a bulky and heavy structure. In spinal surgery, it is desirable to provide a light weight implant that impacts on the surrounding tissue as little as possible. Consequently, it is desirable to have a bone screw with a low profile with respect to both height and width. It is also preferable to limit the width profile of the bone screw to provide more room to work along a rod or other implant in which many elements may be required in a relatively small space.

Furthermore, it is desirable to maintain the number of parts of the device at a minimum. Also, it is desirable to secure the various parts together in such a way, so that, if parts become loose under use for some reason, the device will not totally disassemble.

SUMMARY OF THE INVENTION

The present invention provides an improved polyaxial head bone screw assembly for use in conjunction with spinal surgery and, in particular, for implanting into a bone and securing other medical implants to the bone. The polyaxial bone screw assembly includes a threaded shank member for threaded placement in a bone, a head member connecting to another implant such as a spinal fixation rod and capturing a capture end of the shank member, and a retainer sphere or retainer ring to capture and retain the capture end of the shank member within the head member. The shank member and head member may be set in a plurality of angular relationships with respect to each other within a range of obtuse angles.

The shank or shank member has an outer portion which is threaded, sized and shaped so as to be adapted to be operably screwed into a vertebral body in the spine of a patient. An end of the shank opposite the threaded lower portion includes a frusto-conical capture structure which diverges in diameter in a direction away from the threaded end of the shank. A top of the conical capture end is provided with apertures or formations for non-slip engagement by an installation tool to enable the shank to be threaded into a bone, such as a vertebra. Beyond the conical structure, a knurled dome is provided for positive interfering or cutting engagement by the surface of a rod which is to be clamped and supported by the bone screw assembly.

The head member is generally partially cylindrical in outer shape and has a central axial bore to receive the capture end of the threaded shank and a central U-shaped cradle opens in a direction opposite the axial bore to receive a spinal fixation rod and presents a pair of spaced apart arms. An interior of each of the arms includes threads to receive a threaded plug to secure the rod within the cradle and to clamp the rod into engagement with the knurled dome of the shank to fix the angular position of the head with respect to the shank. The head includes a lower partially spherical socket or seat at the lower end of the axial bore for receiving the ring and forms a neck for surrounding the shank during usage.

The retainer ring has an outer surface which is partially spherical and which is sized and shaped to fit within and swivel within the seat until locked in position, as noted below. The ring also has a central bore which is frusto-conical and of a shape which is compatible with the capture end of the shank to snugly receive the shank therein. The ring is sized to be too large in width to fit through the neck at the bottom of the head when in operable position and is either loaded from the top of the head or through other structure formed in the head. The ring is resiliently expandable to enable the ring to be snapped over the capture end of the shank to retain the capture end within the head member. The head has an assembly or orientation cavity therein which communicates with the U-shaped cradle and which is positioned and sized to enable proper orientation of the retainer ring and engagement of it with the capture end of the shank. The assembly cavity is spaced axially above the seat and neck and has a slightly larger partial spherical diameter than the seat so as to allow the ring to expand during insertion of the shank capture end and then return to a smaller diameter for snugly fitting in the seat. The spherical seat initially forms a pivot bearing with the retainer ring, when no axial downward force is applied to the shank and ring, to retain the capture end of the shank within the head and to enable pivoting the shank relative to the head throughout a limited range. The retainer ring is formed of a resilient or springy material and in a preferred embodiment has a radial split to enable expansion of the diameter of the ring and, particularly, to enable expansion of the diameter of the central bore to enable placement on the conical capture end of the shank.

Once the ring is on the shank and located in the seat in a position suitable to the surgeon with a rod received in the head channel, a closure plug is screwed into the threads between the arms so as to engage the rod and urge the rod under pressure into engagement with the dome on the shank. This in turn urges the spherical surface on the ring into frictional engagement with the spherical surface of the seat so as to lock the rotational position of the shank relative to the head. The dome of the shank is preferably radiused so that it engages the rod in the same manner no matter what alignment is formed between the head and the shank. The dome also preferably has a radius that is substantially less than the radius of the partial spherical surface of the ring. This reduces the required height of the head in comparison to the dome that is a continuation of the spherical surface.

Preferably, the shank feeds into the head from below through the neck of the head and has a smaller diameter in the region of the capture end than the diameter of the threads. This allows the shank to have a comparatively wide and normal thread for screwing into the bone that may be wider than the neck of the head, while also allowing the top of the shank to pass through the neck of the head to connect with the retainer ring.

In the present invention, because the retainer or retainer ring is wider than the width of the rod receiving channel in the head, the ring is preferentially less in height than the width of the channel such that the ring is turned sideways for loading and then turned again a quarter turn to reposition the ring in the head cavity to receive the shank. For a comparable head designed to receive a rod of a certain diameter this allows the retainer to have a greater width. This, in turn, allows the opening through which the shank passes to have a greater diameter and still block passage of the retainer. Because the diameter of the opening is greater, the diameter of the neck and capture end of the shank can also be sized greater allowing for greater strength and optionally allowing the shank to be cannulated or axially bored to provide for use of a guide wire.

In an alternative embodiment, the shank capture end is an axially aligned cylinder that is received through a lower opening in the head. A shank capture member or retainer is generally spherical in shape and has at least a lower partial spherical surface for rotatably engaging a mating surface in a cavity of a head of the bone screw. The spherical shaped retainer has a pair of diametrically opposed side bores that intersect with a bore that receives the shank capture end and which provide for the use of a crimping or deforming tool to pass through the retainer side bores so as to engage and deform the shank capture end.

The deformation of the shank capture ends interferes with removal of the retainer and locks or joins together the shank and retainer so that a main body of the shank protrudes outward from the opening in the bottom of the head and the retainer remains in inside the head on the opposite side of the head lower opening which has a smaller diameter than the portion of the retainer that engages the cavity at the head lower opening, swivelably rotatably securing both the retainer and shank to the head to allow a surgeon to position the head to receive the rod. A bore in the top of the retainer has faceted sides that produce a hex or other shaped opening for receiving a tool for driving the bone screw into a bone or removing the bone screw. The retainer and shank are further locked against rotation when a closure is used to apply pressure to a rod member received in the head which in turn applies pressure to the retainer and frictionally locks the position of the retainer in the cavity and the relative position of the shank to the head.

OBJECTS AND ADVANTAGES OF THE INVENTION

Therefore, the objects of the present invention include: providing an improved bone screw assembly for implantation into a vertebra of a patient wherein the head of the bone screw is swingable or swivelable about an end of a shank of the bone screw until a desired configuration is obtained after which the head is lockable in position relative to the shank; providing such a screw assembly including a threaded shank with a capture end, a head member with a shank receiving bore and a U-shaped rod cradle for receiving a spinal fixation rod, a resiliently expandable shank retainer or retainer ring to retain the capture end of the shank within the head, and a threaded plug receivable in the head to engage a cradled rod and urge it into securing engagement with the capture end of the shank to fix the angular position of the shank relative to the head; providing such a screw assembly wherein the head member includes an internal partial spherical cavity, socket or seat and the retainer ring includes at least a partial spherical outer surface to enable swiveling and universal positioning of the shank relative to the head member from side to side and front to rear within a limited range; providing such a screw assembly in which the head member includes an assembly or orientation cavity above the seat to enable expansion of the ring during joining with the shank and proper orientation of the retainer ring; providing such a screw assembly in which the retainer ring has a radial split to enable resilient expansion and retraction of the ring for snapping the ring onto the capture end of the shank; providing such a screw assembly in which the capture end of the shank is frusto-conical, diverging in diameter in a direction away from the threaded part of the shank and in which the retainer ring has a central bore which is compatibly frusto-conical in shape; providing such a screw assembly in which the capture end of the shank has a knurled dome for positive, interfering engagement by a spinal fixation rod clamped within the assembly and wherein the dome has a radius that is smaller than the radius of the ring partial spherical surface; and providing an alternative bone screw utilizing a generally spherical retainer with a bore for receiving a capture end of an associated shank after which the shank capture end is deformed so as to interferingly secure the shank to the retainer; and providing such a polyaxial head bone screw which is economical to manufacture, which is convenient and secure in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is an exploded perspective view of elements of the bone screw at a reduced scale and illustrates a threaded shank member, a head member, and a retainer ring.

FIG. 3 is an enlarged cross sectional view of the screw head and illustrates the orientation of the split retainer ring for insertion into the head.

FIG. 4 is a view of the screw head similar to FIG. 3 and shows the orientation of the retainer ring to prepare for insertion of a capture end of a threaded shank.

FIG. 5 is a view similar to FIG. 3 and shows the retainer ring about to be snapped onto the capture end of the threaded shank.

FIG. 6 is a view similar to FIG. 3 and shows the retainer ring positioned on the capture end of the threaded shank.

FIG. 7 is a view similar to FIG. 3 and shows the capture end of the shank with the installed retainer ring positioned in a spherical pivot seat of the screw head.

FIG. 8 is a view similar to FIG. 3 and shows the threaded shank with retainer ring pivoted to a selected angle relative to the screw head.

FIG. 9 is an exploded perspective view of a second embodiment of a polyaxial bone screw in accordance with the present invention, showing a shank, a head and a partial spherical retainer.

FIG. 10 is an enlarged cross-sectional view of the head of the second embodiment, taken along line 10-10 in FIG. 11.

FIG. 11 is an enlarged top plan view of the head of the second embodiment.

FIG. 12 is an enlarged cross-sectional view of the head of the second embodiment, taken along line 12-12 in FIG. 11.

FIG. 14 is an enlarged and fragmentary cross-sectional view of the shank, head and retainer of the second embodiment with a crimping tool being utilized to deform the shank to interferingly secure the retainer and shank together.

FIG. 15 is a view similar to FIG. 14, but with the shank lowered relative to the head and with the retainer seated in a partial spherical chamber of the head allowing rotation of the shank and retainer relative to the head.

FIG. 16 is an enlarged and fragmentary view of the shank, head and retainer, taken along a line similar to line 10-10 of FIG. 11 and showing elements in the same position as FIG. 15.

DETAILED DESCRIPTION OF THE INVENTION

Figure 1:
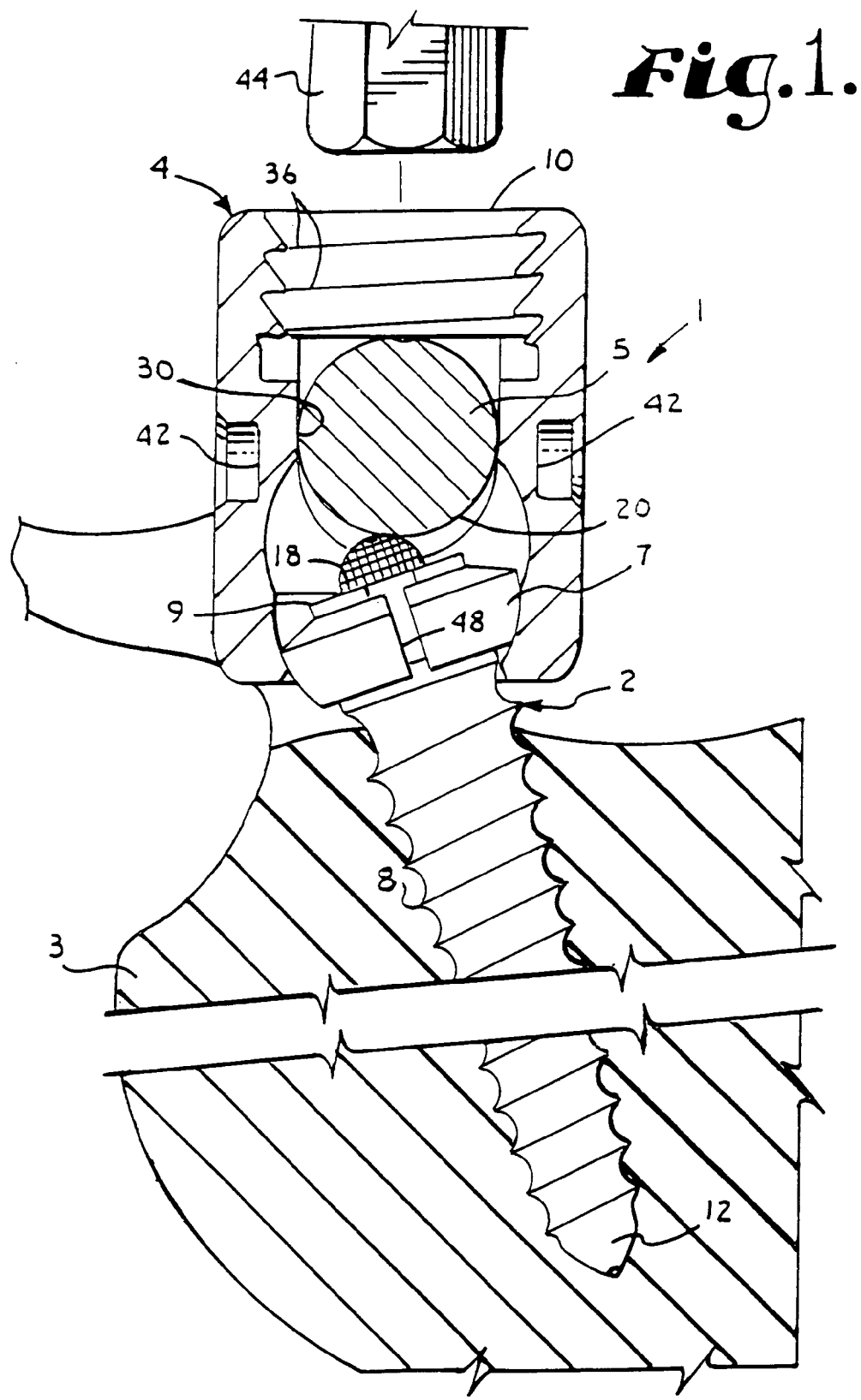
FIG. 1 is an enlarged cross sectional view of a polyaxial head screw with a split retainer ring which embodies the present invention, shown assembled with a rod to hold the rod and inserted in a vertebral bone.
Figure 13:
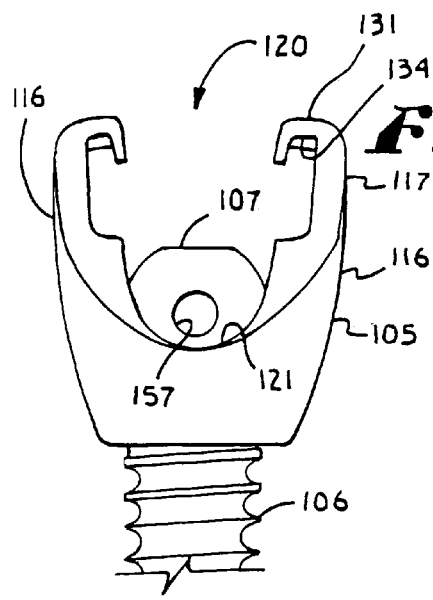
FIG. 13 is an enlarged and fragmentary side elevational view of the shank, head and retainer of the second embodiment, showing the retainer being placed on the shank and raised relative to the head.
Figure 17:
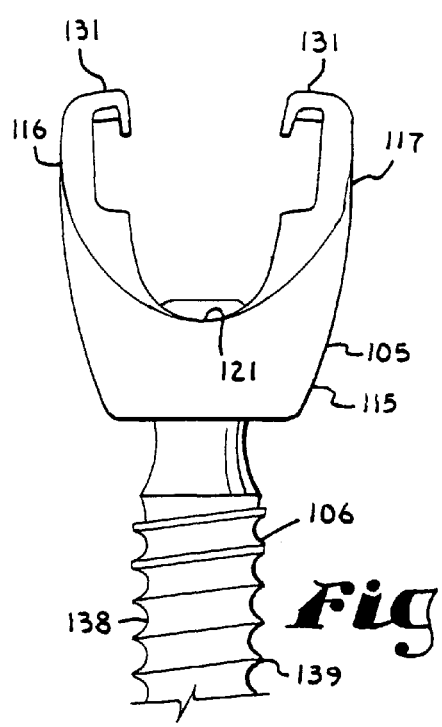
FIG. 17 is an enlarged and fragmentary side elevational view of the shank, head and retainer, assembled as in FIG. 15.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a polyaxial bone screw arrangement which embodies the present invention. The arrangement 1 includes a threaded shank member 2 for threadably implanting into a bone 3, such as a vertebra, and a head member 4 which connects with the shank member 2 to engage and secure a rod member 5, such as a spinal fixation rod, relative to the bone 3. The arrangement 1 also includes a retainer or retainer ring 7 operably positioned within head 4 and engaging a capture end 9 of the shank 2 opposite a region having a thread 8 to retain the capture end 9 within the head 4. The arrangement 1 further includes a plug or closure member 10 which urges the rod 5 into engagement with the capture end 9 of the shank 2. The head 4 and shank 2 cooperate in such a manner that the head 4 and shank 2 can be secured at any of a plurality of obtuse angles, relative to one another and within a selected range of angles both side to side and front to rear, to enable flexible engagement of the arrangement 1 with a rod 5.

Referring to FIGS. 1, 2, and 5, the shank 2 is elongated and is sized and shaped to be screwed into one of the vertebra 3. The shank 2 includes the external helically wound thread 8 that extends from an outer tip 12 to near the capture end 9. On the illustrated shank 2, the capture end 9 includes a region that is frusto-conical in shape, diverging in diameter in a direction away from the outer tip 12 and that is coaxially aligned with an axis of the shank 2. The illustrated capture end 9 has a maximum radius that is substantially less than a radius associated with the shank thread 8 and further, preferably less than the radius of a body 13 of the shank 2 in the region whereupon the thread 8 is located.

The capture end 9 has a plurality of tool engageable grooves, apertures or the like 14 to enable positive engagement by an appropriately shaped installation tool (not shown) to thread and drive the shank 2 into the vertebra 3. An upper end surface 16 of the capture end 9 opposite the tip 12 is provided with a formation or dome 18 to be positively and interferingly engaged by the rod 5 when the assembly 1 is assembled into place. The illustrated shank 2 includes the dome 18 which is radiused and knurled and that centered on the upper end surface 16 of the shank capture end 9 so as to be coaxial with the remainder of the shank 2. The scoring or knurling of the dome 18 operably frictionally abuts against a cylindrical surface 20 of the rod 5, when the plug 10 is tightened to provide non-slip engagement of the shank 2 relative to the rod 5 and to thereby help maintain a desired angular relationship between the shank 2 and the head 4. In certain embodiments, the purpose of the dome 18 is simply to be engaged by the rod 5 during assembly and pushed in such a manner as to frictionally engage the ring 7 with the head 4 as described below. Preferably, the dome 18 is radiused so that the dome 18 engages the rod at the same location even as the head 4 is swivelled relative to the shank 2. However, in certain embodiments the dome 18 could have other shapes.

Referring to FIGS. 2-8, the head member 4 is generally cylindrical in external profile and has a central and axially aligned shank receiving bore 24 ending at an inner and lower neck 26. The neck 26 is radiused to receive the shank capture end 9 and preferably smaller than the radius of the shank body 13 and thread 8. The bore 24 is also preferably sized larger than the capture end 9 of the shank 2 to enable the shank 2 to be oriented through a range of angular dispositions relative to the head 4. The bore 24 may be conically counterbored or beveled in a region 28 to widen the angular range of the shank 2.

The head 4 is provided with a U-shaped rod cradle 30 which is sized to receive the rod 5 therethrough. The illustrated cradle 30 is rounded and radiused at an inner or lower portion 31 to snugly mate with the surface of the rod 5 and open at an outer end 33, with spaced apart parallel side surfaces 32 so as to form upstanding and spaced apart arms 35 with inwardly facing threading thereon. The side surfaces 32 have mating and guide structures 34 formed thereinto which are complementary to mating and guide structures 36 of the closure plug 10 (FIG. 1). The structures 34 and 36 may be helically wound flanges or threads which advance the plug 10 into the head 4, as the plug 10 is rotated about its axis. It is foreseen that structures 34 and 36 may be V-shaped threads, buttress threads, reverse angle threads, or other types of threads or interlocking helically wound flange structure such as is sold under the U.S. registered trademark FLANGE-FORM. Preferably, the structures 34 and 36 are of such a nature as to resist splaying of the arms 35 when the plug 10 is advanced into the cradle 30.

As seen in FIGS. 3 and 4, the head 4 has an assembly cavity 38 formed therein which opens into the cradle 30. A partially spherical socket or seat 40 communicates between the assembly cavity 38 and the shank bore 24 and has a radius that is slightly less than the radius of the assembly cavity 38 that is located axially directly thereabove. The purposes for the cavity 38 and seat 40 will be detailed further below. The head 4 may include external, closed end grip bores 42 for positive engagement by a holding tool (not shown) to facilitate secure gripping of the head 4 during assembly of the arrangement 1. The seat 40 has a spherical radius and extends upward coaxially through the head 4 from the neck 26 to the cavity 38.

The closure plug 10 is generally cylindrical in shape and is provided with a break-off head 44 which is connected to the plug 10 by a weakened area such that the head 44 separates from the plug 10 at a predetermined torque applied to the head 44 during assembly. The illustrated break-off head 44 has a hexagonal cross section for engagement by a tool (not shown) of a complementary shape.

The retainer ring 7 is used to retain the capture end 9 of the shank member 2 within the head member 4. The retainer ring 7 resiliently expands and contracts to enable the ring 7 to be snapped over and seated on the capture end 9 of the shank 2. The ring 7, like the remainder of the arrangement 1, is preferably formed of a material such as a spring stainless steel, tantalum, titanium or other resilient implantable material. The illustrated ring 7 has a radial split 48 which allows the ring 7 to expand in circumference to fit over the capture end 9. Alternatively, other configurations of the ring 7 are envisioned to enable such expansion and retraction of the ring 7. The ring 7 has a central conical bore 50 which is conically shaped to be compatible with the conical shape of the capture end 9. The ring 7 has an outer surface 52 which is frusto-spherical, partially spherical, or a segment of a sphere, and which has a spherical radius approximately equivalent to the spherical radius of the spherical seat 40 within the head 4 and smaller than the radius of the cavity 38. The ring surface 52 also has a radius substantially greater than the dome 18.

FIGS. 3-8 illustrate step by step assembly of the components of the bone screw arrangement 1. In FIG. 3, the ring 7 is inserted into the head 4 through the interior of the U-shaped cradle 30. The ring 7 is oriented with its axis at a right angle to the axis of the bore 24 and to the side surfaces 32 of the cradle 30. FIG. 4 illustrates the ring 7 oriented with its axis parallel or coincident with the axis of the bore 24 and neck 26, by rotating the ring 7 within the assembly cavity 38. In FIGS. 5 and 6, the capture end 9 of the shank 2 is inserted through the bore 24 and engaged with the retainer ring 7 so as to snap the ring 7 over the capture end 9. This is accomplished by pressing the shank 2 into the head 4, causing the ring to engage a constriction at the top of the assembly cavity 38. The relative resistance encountered by the ring 7 allows the capture end 9 to expand the circumference of the retainer ring 7, by expansion of the split 48, so that the capture end 9 enters the central bore 50 of the ring 7. The capture end 9 includes a shoulder 56 which limits penetration of the capture end 9 into the retainer ring 7, as shown in FIG. 6.

FIG. 7 shows the arrangement 1 with the retainer ring 7 lowered from the assembly position and positioned in the spherical seat 40 and the central axis of the shank 2 coaxial with the central axis of the head 4. FIG. 8 shows the shank 2 angled relative to the head 4. The spherical seat 40 and spherical outer surface 52 of the retainer ring 7, when seated in the seat 40, allows universal angular positioning of the shank 2 relative to the head 4 within a limited range, as is shown in FIG. 8. The retainer ring 7, thus, performs the double functions of preventing the capture end 9 of the shank 2 from slipping through the neck 26 and, in conjunction with the seat 40, forms a ball joint for relative orientation of the shank 2 and head 4.

Under some circumstances, it may be desirable to assemble the shank 2 and head 4, prior to threading the shank 2 into the vertebra 3 or other bone. Thereafter, the shank 2 may be conveniently screwed into the vertebrae 3 by passing the installation tool through the cradle 30 to engage the grooves 14 of the capture end 9. The vertebra 3 may be predrilled with a pilot hole or the like (not shown) to minimize stressing the bone 3. Once the shank 2 has been threaded to its desired depth, the head 4 can be oriented as desired. The rod 5 is positioned in the cradle 30, engaging the knurled dome 18, and the closure plug 10 is advanced into the head 4 to clamp the rod 5 between the capture end 9 and the closure plug 10. When the preset torque limit of the plug 10 is reached, the break-off head 44 separates from the closure plug 10. The force transmitted by torquing of the closure plug 10 transmits through the rod 5 and through the dome 18 to the ring 7. The partial spherical surface 52 of the ring 7 is thereby urged into tight frictional relationship with the partial spherical surface 40 of the head 4, thereby locking the angular configuration of the head 4 relative to the shank 2.

The reference numeral 100 generally represents a second embodiment of a bone screw shown in FIGS. 9 through 20 in accordance with the present invention for implanting in a vertebra 101 or other bone.

The bone screw 100 includes a head 105, a shank 106, a retainer or capture sphere 107 and a closure 108. The bone screw 100 also operably receives a rod member 110 that is part of an implanted assembly.

The head 105 has a lower body 115 with a pair of upstanding and spaced arms 116 and 117. The arms 116 and 117 are spaced sufficiently to form a channel 120 that is sized and shaped to snugly receive and subsequently secure the rod member 110 to the bone screw 100. In this manner the channel 120 opens upward and sideways outwardly to opposed sides of the head 105. The head 105 has a central axis indicated by the reference letter A. The channel 120 has a pair of lower spaced curved surfaces 121 that preferably have substantially the same radius as the rod member 110.

An axially centered chamber 122 is located in the head 105 below the channel 120 and opens upwardly into the channel 120. The chamber 122 has a surface 125 that is sized and shaped to snugly but slidably receive the sphere 107. In particular, a lower portion or hemispherical seat 126 of the chamber surface 125 is curved or hemispherical so as to have substantially the same radius as the sphere 107.

An axially aligned bore 129 communicates between the chamber 122 and a lower exterior of the head 105. The bore 129 has a smaller diameter than the sphere 107, so as to prevent passage of the sphere 107 through the bore 129.

The arms 116 and 117 include inwardly facing flanges 131 with downward extending ears 132 at outer ends thereof. The flanges 131 and ears 132 collectively form curved channels 134 that receive the closure 108, as described below. Tool gripping indents 135 are formed on the exterior of the head 105.

The shank 106 is elongate and has a central axis of rotation indicated by the reference letter B. The shank 106 has a lower body 138 with a helically wound thread 139 wrapping thereabout. The shank body 138 is operably threaded into a vertebra 101 in the manner shown in FIG. 18.

The shank 106 has an axially aligned upper portion or capture end 144 with a cylindrically shaped surface 145 is connected to the shank body 138 by a neck 147 and extends upwardly therefrom.

The sphere 107 has an outer generally spherical or at least partially spherical shaped surface 150 that is sized and shaped to be snugly, but rotatably received in the hemispherical seat 126. The sphere 107 has a radial non passthrough bore 155 sized and shaped to snugly, but initially slidably receive the shank capture end 144.

The sphere 107 includes a pair of side opposed bores 157 and 158 which are diagonally aligned and which intersect with and open into the bore 155 so as to be perpendicular thereto. Furthermore, the sphere 107 has an upper drive bore 159 that is coaxial with the bore 155 and that has a polyhedral shaped interior surface 160 that is sized and shaped to receive an allen type driving tool or other suitably shaped tool for driving the shank 106 into the vertebra 101, as described below.

Figures 19, 20:
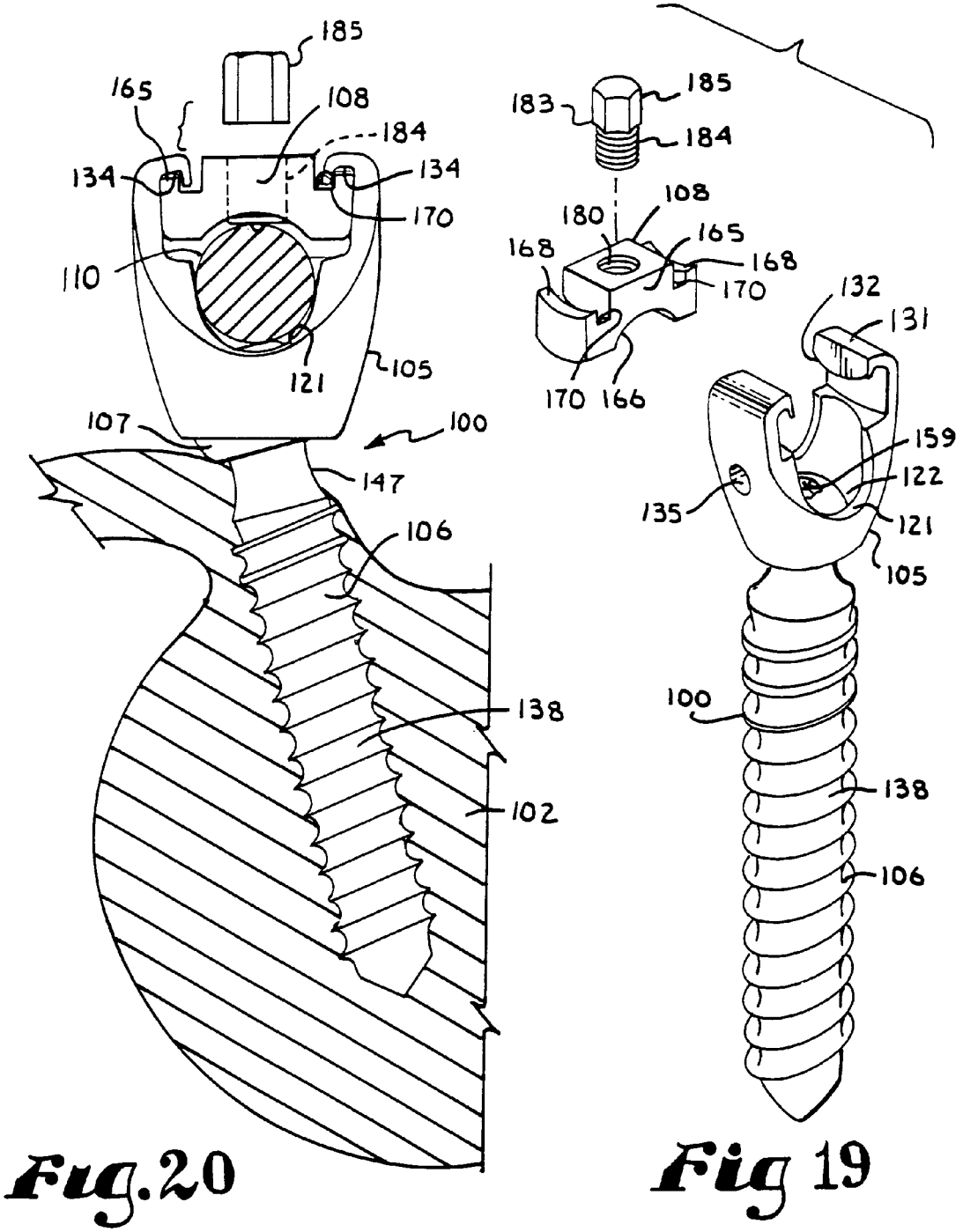
FIG. 19 is an enlarged, exploded and perspective view showing the elements of the bone screw, as seen in FIG. 15 along with a closure and closure set screw.
FIG. 20 is an enlarged front elevational view of the fully assembled bone screw of the second embodiment implanted in a vertebra shown in cross section and showing a break-off head of the set screw having been broken away from a remainder of the set screw.

The closure 108 is seen in FIGS. 20 and 21 and is a "slide in" type device. The purpose of the closure 108 is to close the channel 120 and to secure the rod member 110 in the channel 120 and against movement relative to the head 105. The closure 108 includes a block or saddle 165 with a lower cylindrically shaped surface 166 that is sized and shaped to snugly mate with the rod member 100.

Located on opposite ends of the saddle 165 are a pair of upwardly extending ears 168 that are sized and shaped to be slidingly received in the head channels 134. The ears 168 are spaced from a body 169 of the saddle 165 by respective channels 170 that are curved and sized and shaped to slidingly receive the ears 132 of the head arms 116 and 117. In this manner the ears 132 and 168 overlap when the closure 108 is in the head 105 to resist outward splaying of the arms 116 and 117.

The central body 169 of the closure 108 includes an axially aligned pass through and threaded bore 180. The bore 180 receives a break-off set screw 183 that has a base 184 and a break-off head 185.

The bone screw 100 parts are assembled and used in the following manner. As is seen between FIGS. 9 and 14, the shank upper portion or capture end 144 is inserted through the lower side of the lower side of the head 105 and so as to extend into the chamber 122, while the sphere 107 is inserted or loaded through the channel 120 toward the cavity or chamber 122. The shank upper portion 144 is inserted into the sphere bore 155. While the sphere 107 is maintained raised or in the upper portion of the head 105, a crimping or deforming tool 190 is utilized to deform the shank 106 relative to the sphere 107, so as to lock or secure both to one another. In particular, the tool 190 has arms 191 that can be biased by a scissors action or the like toward one another and a pair of lower cylindrical shaped studs 192 ending in points. The studs 192 are sized and shaped to be inserted through opposed sides of the channel 120 and simultaneously through the side bores 157 and 158 respectively in the sphere 107 so as to engage the shank capture end 144. Pressure is then applied through the studs 192 against the shank 106 so as to produce a deformation 193 that frictionally engages and interferes with the sphere 107 and thereafter prevents removal of the sphere 107 from the shank 106. While deformation is used herein to secure the retainer sphere to the shank, it is also foreseen that the same could be accomplished by threading the parts and screwing them together, by inserting a pin through the parts, by using cleats interlocking with receivers, by welding, by adhering, or by any other suitable mechanism or composition.

Figure 18:
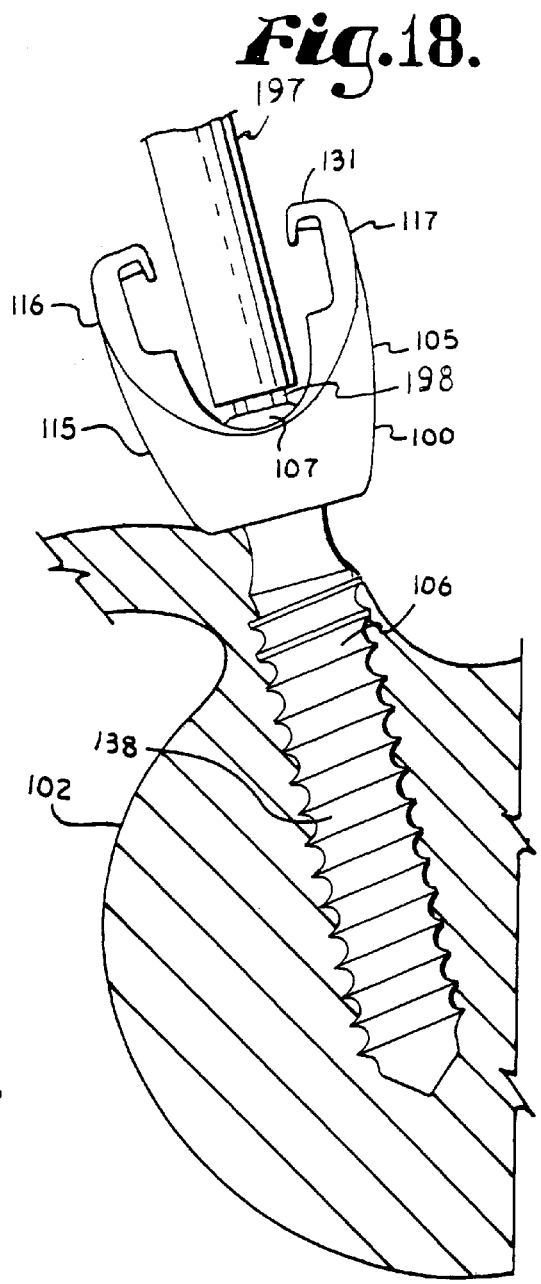
FIG. 18 is an enlarged and fragmentary perspective view of the elements of the bone screw shown in FIG. 17 being driven into a vertebra that is shown in cross-section by a driving tool.

After the sphere 107 is assembled onto the shank 106, a driving tool 197 with a driving head 198 that is sized and shaped to fit the sphere drive bore 159 is used to drive the assembled parts into a bone, such as the illustrated vertebra 102 shown in FIG. 18.

Thereafter, a rod member is inserted into the channel 120. An upper portion of the sphere 107 extends upwardly into the channel 120 such that it is engaged by the rod member 110. The closure 108 is then slid sideways while saddling over the rod member 110 so that the closure ears 168 seat in the head channels 134 inside the head ears 132 and thereby lock the arms 116 and 117 against outward splaying.

The set screw 183 is then inserted into the closure bore 180 and torqued until a preselected torque is reached at which time the set screw head 185 breaks from the body 184, as seen in FIG. 20.

At this time, the set screw 184 exerts pressure against the rod member 110 which in turn exerts pressure against the sphere 107 so that the sphere 107 and attached shank 106 are frictionally locked in place relative to the head 105. In particular, before the set screw 184 is tightened, the head 105 can be rotated or swivelled relative to the shank 106 and sphere 107 assemblage, so as to find an optimal position for insertion of the rod member 110. After the set screw 184 is tightened, the shank 106 and sphere 107 assemblage is locked in position relative to the head 105.

The bone screw 100 can be removed by removing the set screw base 184 after which the closure 108 can be taken from the head 105. The rod member 110 can then be removed from the head 105 and the shank 106 unscrewed from the vertebra 102.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone screw comprising:
   a) a head adapted to receive a rod member in an upper channel thereof; said head having a cavity lower opening to an external surface of said head through said opening; said cavity having an integral partial lower mating surface and an upper larger cavity portion sized and shaped to allow expansion of an expandable retaining ring to capture a shank therein;
   b) a shank having a threaded body and a capture end; said capture end being insertable into said head cavity through said lower opening when said retaining ring is positioned in said cavity;
   c) the retaining ring having capture structure to expandingly receive and capture said shank capture end within the cavity and thereafter contract and polyaxially rotate in conjunction with the shank relative to the cavity during positioning of the shank relative to the head; the shank extending above the retaining ring after the shank and retaining ring are joined in the cavity; said ring having a partial spherical surface that operably seats on said head cavity partial spherical lower mating surface; and d) wherein an upper surface of the shank capture end solely receives a downward force to lock the position of the shank relative to the head.

2. The bone screw according to claim 1 wherein:

a) said head partial spherical lower mating surface is in a first region of said cavity and said cavity includes a second region located axially above said cavity first region; said cavity second region being larger than said cavity first region;

b) said shank capture end causing said retaining ring to expand and contract during connection to said shank, such expansion and contraction operably occurring in said second region and thereafter said retaining ring being seatable in said first region.

3. A polyaxial bone screw for implantation in bone comprising:

a) a shank having a threaded body adapted to be operably received in a bone and a capture end extending upwardly from said threaded body;

b) a head having a channel formed between a pair of arms, said channel opening to an exterior of the head being sized and shaped for operably receiving a rod member; said head having an interior cavity communicating directly with said channel; said head also having a lower opening axially aligned with and communicating with said cavity and opening to a lower side of said head exterior, said lower opening being sized and shaped to receive said shank capture end therethrough;

c) an expandible and contractible ring shaped retainer separate from said shank that is sized and shaped to be slidingly received through said channel and into said cavity; said retainer expandibly receiving and operably capturing said shank capture end in the head cavity and thereafter contracting so as to allow polyaxial rotation of the shank and retainer together relative to the head during positioning of the shank relative to the head, said retainer having an aperture therein for receiving and operably capturing said shank capture end; said retainer having a radial diameter, such that when said retainer is joined to said shank a combination of the joined retainer and shank is too large to allow passage thereof through said head lower opening; said shank projecting above the retainer and into said channel when assembled so as to be adapted to directly engage the rod member when placed in said channel; and d) a closure for closing said channel and adapted to bias against the rod member; said closure being rotatably joined to an interior of said arms by a splay resistant helical wound guide and advancement structure.

4. A polyaxial bone screw for implantation in bone comprising:

a) a shank having a body that is threaded so as to be adapted to be implanted into a bone and an upper capture end extending from said body;

b) a head having a channel adapted to receive a rod member, a lower opening having a radius adapted to receive said shank capture end and a cavity communicating with the channel and the lower opening, said channel, cavity and lower opening being in axial alignment;

c) a an expandible and contractible retainer non integral with said shank and being sized and shaped to be located during use in the head cavity, said retainer expanding around said shank capture end and thereafter contracting to capture said shank capture end; said retainer having an outer radius that is larger than said lower opening radius when said shank capture end is captured by said retainer; and d) said retainer and said shank joining in an assembly unit in the cavity to polyaxially rotate together relative to the head; said shank having an upward axial projection opposite said shank body that extends above the joined retainer; said projection being sized and shaped to extend into said channel during use so as to be adapted to frictionally engage a rod member placed in said channel.

5. A polyaxial bone screw comprising:

a) a head having an upper channel adapted to receive a rod member; said head further having a cavity axially aligned with said upper channel and communicating with said upper channel directly through a first opening into said channel; and said head having a second lower opening axially aligned with said upper channel for communication between said cavity and an exterior of said head; said cavity including a seat with a radiused surface adjacent to said second opening;

b) a shank having an elongate threaded body and a capture end; said capture end being sized and shaped to be received through said head second opening and into said cavity; and c) a reversibly expandable retainer separate from an upper portion of said shank and having capture structure that is sized and shaped to expandibly receive and thereafter contractibly capture said shank capture end in the cavity so as to polyaxially rotate with the shank relative to the cavity and head during positioning of the shank relative to the head; said retainer further having a radiused surface that is sized and shaped to be rotatably received on said radiused surface of said seat and having a width greater than said head second opening; said shank having an upper end that projects above the retainer and into said channel when said capture structure is captured in said head by said retainer so that said shank is adapted to directly engage the rod member when the rod member is positioned in said channel.

6. A polyaxial bone screw comprising:

a) a head having a body and a pair of upstanding arms defining a channel between said arms having a width; said head having a cavity communicating with said channel and having an opening communicating with the underside of said head; said channel, said cavity and said opening being axially aligned, and said cavity having a first radiused surface;

b) a shank having an elongate threaded body for implantation into a bone and a capture end opposite said body that when the shank is placed through said opening and in the head extends into the channel; and c) a retainer separate from the shank and having a structure sized and shaped to expandibly receive and contractibly capture said shank capture end so as to join with the shank in the cavity and, thereafter, polyaxially rotate relative to the cavity and head during positioning of the head relative to the shank; said retainer having a second radiused surface that is sized and shaped to be rotatably received on said cavity first radiused surface; said retainer second radiused surface having a diameter that is greater than said channel width; said shank extending above said retainer when joined; said retainer having a height that is less than said channel width so as to allow said retainer to pass sideways through said channel and into said cavity.

7. The bone screw according to claim 6 wherein:

a) said retainer is generally hemispherical in outer shape.

8. The bone screw according to claim 6 including:
a) a locking mechanism for securing said shank to said retainer.

9. The bone screw according to claim 6 wherein:
a) said opening is smaller in diameter than said retainer radiused surface.

10. The bone screw according to claim 6 in combination with:
a) a rod member operably received in said channel and engaging said retainer to urge said retainer into frictional engagement with said cavity;
b) a closure for operably closing between said arms and applying force to said retainer through said rod member to operably lock a position of said shank relative to said head.

11. The bone screw according to claim 10 wherein:
a) said closure includes guide and advancement structure that joins with mating structure on said arms to guide said closure on rotation thereof.

12. The bone screw according to claim 11 wherein:
a) said guide and advancement structure inhibits splaying of said arms.

13. The bone screw according to claim 12 wherein:
a) said guide and advancement structure includes reverse angle threads.

14. The bone screw according to claim 12 wherein:
a) said guide and advancement structure is an interlocking structure.

15. A polyaxial bone screw comprising:
a) a head having a body and a channel adapted to receive a rod member; said channel being positioned between a pair of arms and having a width; said head having a cavity below said channel and a lower opening between an exterior of said head and said cavity;
b) a shank having an elongate threaded body that has a first radial diameter at the widest location therealong; said shank having a capture end opposite said body;
c) an expandible and contractible retainer separate from the shank and being operably sized and shaped to expand so as to receive the shank capture end and thereafter contract so as to capture said shank capture end so as to be joined with the shank within the cavity and, thereafter, polyaxially rotate with the shank relative to the head and cavity during positioning of the shank relative to the head; said retainer being operably received and swivable within said cavity with the shank extending above the retainer; and whereby:
d) said shank diameter is larger than said channel width such that said shank cannot pass through said channel; said shank capture end being sized and shaped to pass through said head lower opening and be received into said retainer within said cavity and being sized and shaped to extend upwardly and receive downward pressure from the rod when the rod is placed in the channel without the retainer receiving downward pressure directly from the rod during assembly but rather from the rod through the shank.

16. A polyaxial bone screw comprising:
a) a head having a channel adapted to receive a rod and said channel having a side to side width; said head having an internal cavity communicating with said channel; said head having a lower opening into said cavity from an exterior of said head; said channel, said cavity and said lower opening being in axial alignment;
b) a shank that is swivable relative to said head during assembly and positioning of the shank relative to the head and further being adapted to be later lockable; said shank having an upper capture portion and a lower threaded portion; the shank capture portion extending upwardly so as to receive downward pressure from a rod placed in the channel during assembly;
c) an expandible and contractible retainer separate from the shank that is sized and shaped to expand around said shank capture portion and then contract so as to capture said shank capture portion and so as to join therewith and, thereafter, polyaxially rotate together with the shank relative to the head during the positioning of the shank relative to the head and operably located in said cavity;
d) said shank lower threaded portion having a diameter that is larger than said channel width so as to prevent said shank from passing therethrough such that said shank must enter said cavity through said lower opening to join with said retainer.

17. The bone screw according to claim 16 wherein:
a) said retainer having a height less than a radial diameter thereof; said retainer diameter being too large to fit through said channel when turned so as to receive said shank capture end, such that said retainer must be turned sideways to pass through said channel and then rotated so as to be aligned to receive said shank capture end in said cavity.

18. In a polyaxial bone screw having a bone implantable shank, a head and a retainer for capturing an end of said shank; the improvement comprising:
a) said head having a channel adapted to receive a rod said channel being sized and shaped to have a width somewhat larger than the rod; and
b) said retainer separate from the shank and being located in a cavity in said head that communicates with said channel such that said retainer is loaded into said cavity through said channel; said retainer having a radial diameter larger than said channel width such that said retainer must be loaded sideways through said channel and into said cavity and then turned a quarter turn to so as to be able to expand and receive said shank capture end and then contract so as to join with the shank and thereafter polyaxially rotate with the shank relative to the head; the shank extending above the retainer so that the shank and not the retainer initially receives pressure from the rod during assembly to lock a position of the shank relative to the head.

19. In a polyaxial bone screw having a threaded shank, a head and a retainer wherein the retainer is received in said head and expanded around said shank and then contracted so as to be joined to said head and thereby to allow said shank to be swivelably joined to said head for placement of said head; said head having a channel adapted to receive a rod; the improvement comprising:
a) said channel having a width that is substantially limited to a width of the rod to be fully received by said head channel; and
b) said shank is upwardly loaded into said head and when fully loaded extends above the retainer so as to be able to receive a downward pressure from above;
c) said retainer is separate from the shank and is received in the head through said channel and has a width that is greater than said channel width such that said retainer must be loaded into said head at least partially sideways and then turned to so as to be able to expand and receive said shank through a lower opening in said head; said lower opening having a diameter less than a width of said retainer; the shank and the expanded retainer being joined in the head by the expanded retainer contracting around the shank and, thereafter, polyaxially rotating together relative to the head during positioning of the head relative to the shank;

d) whereby because the retainer width is larger than said channel width, the diameter of said lower opening is proportionally, relative to rod size, sized larger to allow said shank to be sized larger for increased strength and to allow cannulation.

20. In a polyaxial bone screw having a head adapted to receive a rod member, a shank and a reversibly expandable retainer that is non-integral with said shank for capturing said shank in said head by expanding around said shank and then contracting around said shank so as to be joined with said shank; the improvement being:

a) said shank, after joining with the retainer, extending above the retainer and having an upward projection that is adapted to initially receive a downward force from above and wherein said projection has a height that is less than a radius of said retainer and the wherein said shank and the retainer polyaxially rotating together relative to the head during positioning of the head relative to the shank.

21. In a polyaxial bone screw having a head with a channel adapted to receive a rod member, a shank and a reversibly expandable retainer that is non-integral with said shank and that expands and then contracts around said shank so as to capture said shank in said head, said retainer having a radius; the improvement wherein:

a) said shank has an upward projection that extends above the retainer a predetermined height after being contractibly captured; wherein the height is less than the retainer radius; the shank and the retainer polyaxially rotating together relative to the head during positioning of the head relative to the shank.

22. A polyaxial bone screw and rod combination comprising:

a) a shank having a lower threaded end for implanting in a bone and an upper capture end;

b) a head having a cavity for operably receiving said shank capture end;

c) a reversibly expandable capture structure associated with said shank to reversibly expand around said shank capture end so as to form an assembly in said cavity and capture said capture end within said cavity; said assembly polyaxially rotates with the shank relative to the head and cavity during positioning of the head relative to the shank;

d) the shank extending above the capture structure and said head including a pair of spaced upwardly projecting arms forming a channel therebetween sized and shaped to receive a rod; said channel being sized and positioned such that said rod initially applies downward pressure only through said shank capture end so as to bias said assembly against said head so as to lock said shank in a fixed position relative to said head; and e) a closure for closing between said arms and urging said rod downward; said closure being rotatably joined to said arms by first and second splay resisting mating guide and advancement structures on said closure and arms respectfully.

23. The combination according to claim 22 wherein:

a) said mating guide and advancement structures are helically wound and interlocking.

24. A polyaxial bone screw comprising:

a) a head having a channel adapted to receive a rod member; said head further having a cavity communicating directly through a first opening into said channel and having a second lower opening communicating with an exterior of said head; said cavity including a seat with a seat radiused surface; said channel, said first opening, said cavity, said second opening and said seat being axially aligned;

b) a shank having an elongate threaded body and a capture end; said capture end being sized and shaped to be received through said head second opening and into said cavity; and c) a reversibly expandable retainer separate from said shank and having capture structure that is sized and shaped to expand, receive and capture said shank capture end in the cavity so that the shank and said retainer thereafter polyaxially rotate together relative to the head during positioning of the head relative to the shank; said shank extending above the retainer after being joined together; said retainer further having a retainer radiused surface that is sized and shaped to be rotatably received on said radiused surface of said seat and said retainer having a diameter greater than a diameter of said head second opening;

d) said head having a head body containing said cavity and a pair of spaced arms extending upward from said head body, said arms being located on opposite sides of said channel;

e) said arms having a spacing that is less than twice the radius of said retainer radiused surface; said retainer being a partial sphere and being sized and shaped to pass sideways through said channel; said cavity being sized and shaped to allow said retainer to rotate therein to allow said retainer to align with, reversibly expand and receive said shank capture end while in said cavity with an upper end of the shank capture structure extending above said retainer so as to be able to initially receive a downward pressure from a rod positioned in the channel during assembly, the pressure being transferred to the retainer from the shank to frictionally lock the retainer and the shank in position relative to the head.

25. A polyaxial bone screw comprising:

a) a head adapted to receive a rod member, including:

i) a pair of spaced upstanding arms forming an upper channel for receiving the rod member, each of the arms having an interior first guide and advancement structure;

ii) a cavity located below the arms and having integral upper and lower portions, the upper portion being located axially above the lower portion and having a width greater than a width of the lower portion, and the lower portion having an integral partially spherical seating surface; and iii) a lower opening joining the lower portion with a lower external surface of the head;

b) a shank having i) a threaded body; and ii) a capture end extending upwardly from the body and insertable into the head cavity through the lower opening; the shank capture end being sized, shaped and positioned to be adapted to initially solely receive a downward force when a rod member is received in the head upper channel;

c) an expandible retaining ring receivable in the cavity and joinable with the shank capture end, and including:

i) a ring capture structure to operably receive and capture the shank capture end within the upper cavity portion, wherein the upper cavity portion width is sized so as to allow expansion of the retaining ring during joining of the shank capture end with the retaining ring; the shank capture end causing the retaining ring to expand and contract during connection to the shank, such expansion and contraction operably occurring in the cavity upper portion and thereafter the retaining ring being seatable on the spherical seating surface; wherein ii) the shank extends above the retaining ring after the shank capture end and the retaining ring are joined in the head cavity; and d) a closure having a second guide and advancement structure thereon for helically mating with the first guide and advancement structure upon rotation thereof; the closure adapted to advance downwardly and lock the polyaxial screw upon rotation in the head; the first and second guide and advancement structure being resistant to splay of the arms.

26. In a polyaxial bone screw having a threaded shank, an expandible head and a retainer wherein the retainer is received in the head and expanded around the shank and then contracted so as to be joined to the head and thereby to allow the shank to be swivelably joined with respect to the head; the head having a channel adapted to receive a rod and a lower opening; the improvement comprising:

a) the channel having a width that is somewhat wider than that of the rod to be fully received by the head channel; and b) the shank is upwardly loaded into the head through the lower opening and when fully loaded extends above the retainer so as to be able to initially solely receive a downward pressure from above; wherein c) the lower opening has a width less than the a width of the retainer; the shank and the expandible retainer are joined in the head by the retainer contracting around the shank and, thereafter, polyaxially rotating together relative to the head during positioning of the head relative to the shank.

* * * * *